US007425539B2

(12) United States Patent
Donovan et al.

(10) Patent No.: US 7,425,539 B2
(45) Date of Patent: Sep. 16, 2008

(54) FACTOR IXA FOR THE TREATMENT OF BLEEDING DISORDERS

(75) Inventors: Shane Donovan, Los Angeles, CA (US); Donald A. Baker, Thousand Oaks, CA (US)

(73) Assignees: Baxter International Inc., Deerfield, IL (US); Baxter Healthcare S.A., Wallisellen, Zurich (CH)

( * ) Notice: Subject to any disclaimer, the term of this patent is extended or adjusted under 35 U.S.C. 154(b) by 0 days.

(21) Appl. No.: 11/068,596

(22) Filed: Feb. 28, 2005

(65) Prior Publication Data

US 2005/0209149 A1 Sep. 22, 2005

Related U.S. Application Data

(60) Provisional application No. 60/554,726, filed on Mar. 19, 2004.

(51) Int. Cl.
*A61K 38/00* (2006.01)
(52) U.S. Cl. .............................. 514/12; 514/2; 435/7.1
(58) Field of Classification Search ................. None
See application file for complete search history.

(56) References Cited

U.S. PATENT DOCUMENTS

| | | | |
|---|---|---|---|
| 3,560,475 A | 2/1971 | Fekete et al. | |
| 4,286,056 A | 8/1981 | Andary et al. | |
| 4,357,321 A * | 11/1982 | Thomas .................... | 424/94.64 |
| 4,770,999 A | 9/1988 | Kaufmann et al. | |
| 5,171,569 A | 12/1992 | Anson et al. | |
| 5,457,181 A | 10/1995 | Michalski et al. | |
| 5,770,700 A | 6/1998 | Webb et al. | |
| 5,919,909 A | 7/1999 | Josic et al. | |
| 6,037,452 A | 3/2000 | Minamino et al. | |
| 6,586,573 B1 | 7/2003 | Bresman et al. | |
| 6,624,289 B1 * | 9/2003 | Bajaj ......................... | 530/328 |
| 6,649,386 B2 | 11/2003 | Roser | |
| 7,087,723 B2 | 8/2006 | Bresman et al. | |
| 7,247,707 B2 | 7/2007 | Bresman et al. | |
| 2003/0050225 A1 | 3/2003 | Butenas et al. | |
| 2003/0203845 A1 | 10/2003 | Knudsen et al. | |
| 2004/0023333 A1 | 2/2004 | Hauser et al. | |
| 2004/0072757 A1 | 4/2004 | Wolf et al. | |
| 2004/0110675 A1 | 6/2004 | Sheehan | |
| 2004/0235737 A1 | 11/2004 | Barrowcliffe | |

FOREIGN PATENT DOCUMENTS

| | | |
|---|---|---|
| EP | 1 048 735 A1 | 11/2000 |
| EP | 1 260 582 B1 | 11/2004 |
| EP | 1635861 | 3/2006 |
| WO | WO96/00577 A | 1/1996 |
| WO | WO 2004/103397 | 12/2004 |

OTHER PUBLICATIONS

Ahmad, S.S., et al.; "The Role of the Second Growth-Factor Domain of Human Factor IXa in Binding to Platelets and in Factor-X Activation"; *Biochemical Journal*; 310; pp. 427-431 (1995).
Astermark, J.; "Treatment of the Bleeding Inhibitor Patient"; *Semin Thromb Hemost*; 29(1); pp. 77-86 (2003).
Bajaj, S.P.; "Region of Factor IXa Protease Domain that Interacts with Factor VIIIa: Analysis of Select Hemophilia B Mutants"; *Thrombosis & Haemostasis*; 82(2): pp. 218-225 (1999).
Bajaj, S.P., et al.; "Factor IXa:Factor VIIIa Interaction"; *Journal of Biological Chemistry*; 276(19); pp. 16302-16309 (2001).
Choo, K.H., et al.; "Molecular Cloning of the Gene for Human Anti-Haemophilic Factor IX"; *Nature*; 299; pp. 178-180 (1982).
Dusel, C.H., et al.; "Identification of Prothrombin as a Major Thrombogenic Agent in Prothrombin Complex Concentrates"; *Blood Coagulation and Fibrinolysis*; vol. 15, No. 5; pp. 405-411 (2004).
Fair, et al.; "Human Hepatoma Cells Secrete Single Chain Factor X, Prothrombin, and Antithrombin III"; *Blood*; 64(1):194-204 (1984).
Fuchs, H.E., et al,; "Regulation of Factor $IX_a$ In Vitro in Human and Mouse Plasma and in Vivo in the Mouse"; *J. Clin. Invest.*; vol. 73, pp. 1696-1703 (1984).
Gallisti, S., et al.; "Respective Roles of Factors II, VII, IX, and X in the Procoagulant Activity of FEIBA"; *Blood Coagul Fibrinolysis*; vol. 13(7); pp. 653-655 (2002).
Gray, E., et al.; "Measurement of Activated Factor IX in Factor IX Concentrates; Correlation with in Vivo Thrombogenicity"; *Thrombosis & Haemostasis*; 3(4); pp. 675-679 (1995).
Hellstern, P.; "Production and Composition of Prothrombin Complex Concentrates: Correlation Between Composition and Therapeutic Efficiency"; *Thromb. Res.*; Vo. 95(4 Suppl 1); pp. S7-12 (1999).
Himmelspach, M., et al.; "A Fully Recombinant Partial Prothrombin Complex Effectively Bypasses fVIII in vitro and in vivo"; *Thromb. Haemost.*; vol. 88(6); pp. 1003-1011 (2002).
Kurachi, et al.; "Isolation and Characterization of a cDNA Coding for Human Factor IX"; *Proc. Natl. Acad. Sci. USA*; 79:6461-6464 (1982).

(Continued)

*Primary Examiner*—Hope A Robinson
(74) *Attorney, Agent, or Firm*—Townsend and Townsend and Crew LLP

(57) ABSTRACT

The invention provides a method of treating bleeding disorders in a subject by administration of a preparation enriched for Factor IXa. The Factor IXa can be produced by proteolytically activating recombinantly-produced Factor IX. The invention also provides an improved method for producing Factor IXa from a plasma fraction, which method results in a Factor IXa product containing little or no prekallikrein activity, thus reducing the incidence of undesired side effects in a subject.

4 Claims, 5 Drawing Sheets

OTHER PUBLICATIONS

Kusch, M., et al.; "High Sensitivity Detection of Activated Factor IX"; *Thromb. Haemost.*; vol. 79(4); pp. 778-783 (1998).

Lowe, G.D.; "Factor IX and Thrombosis"; *Br. J. Haematol.*; vol. 115(3); pp. 507-513 (2001).

Lundblad, R.L., et al.; "Measurement of Active Coagulation Factors in Autoplex-T with Colorimetric Active Site-Specific Assay Technology"; *Thrombosis & Haemostasis*; 80; pp. 811-815 (1998).

McNeely, T.B., et al.; "The Anticoagulant Mechanism of Action of Heparin in Contact-Activated Plasma: Inhibition of Factor X Activation"; *Blood*; vol. 65, No. 5; pp. 1226-1231 (1985).

Nemerson, Y; "Tissue Factor and Hemostasis"; *Blood*; vol. 71:1, pp. 1-8 (1988).

Philippou, H., et al.; "High Purity Factor IX and Prothrombin Complex Concentrate (PCC): Pharmacokinetics and Evidence that Factor IXa is the Thrombogenic Trigger in PCC"; *Thrombosis & Haemostasis*; l76(1): pp. 23-28 (1996).

Pieters, J., et al.; "Heparin-Stimulated Inhibition of Factor IXa Generation and Faxtor IXa Neutralization in Plasma"; *Blood*; vol. 76:3; pp. 549-554 (1990).

Shord, S.S., et al,; "Coagulation Products and Their Uses"; *Am. J. Health-Syst. Pharm*; vol. 57; pp. 1403-1417 (2000).

Tankersley, et al,; "Activation of Factor XII by Dextran Sulfate: The Basis for an Assay of Factor XII";*Blood*; 62(2):448-456 (1983).

Van Dieijen, G., et al.; "The Role of Phospholipid and Factor VIIIa in the Activation of Bovine Factor X"; *J Biol Chem.*; 256:7; pp. 3433-3442 (1981).

Wojcik, E.G.C., et al.; "Modification of the N-Terminus of Human Factor IX by Defective Propeptide Cleavage or Acetylation Results in a Destabilized Calcium-Induced Conformation: Effects on Phospholipid Binding and Activation by Factor XIa"; *Biochem J*; 323; pp. 629-636 (1997).

Zhong, D., et al.; "First Epidermal Growth Factor-Like Domain of Human Blood Coagulation Factor IX is Required for its Activation by Factor VIIa/ Tissue Factor but not by Factor Xia"; *Proc. Natl. Acad. Sci. USA*; vol. 91; pp. 3574-3578 (1994).

Barrowcliffe, T.W., et al.; "Binding to Phospholipid Protects Factor-VIII from Inactivation by Human Antibodies"; *Journal of Laboratory and Clinical Medicine*; vol. 101, No. 1, pp. 34-43 (1983).

S. Schulman, *Protein Content of Coagulation Factor Concentrates*, "Biotechnology and the Promise of Pure Factor VIII"—Proceedings of the Symposium on Biotechnology and the Promise of Pure FVIII, 1988, Monte-Carlo, pp. 21-30.

Royal A. Mccgraw et al., "Structure and Function of Factor IX: Defects in Haemophilia B", *Clin Haematol*, 1985, pp. 359-383, vol. 14, Issue 2.

* cited by examiner

Autoplex Preparations

Q-sepharose chromatography

Salt elution

Pooled eluate containing Factor IXa

FIXa  25  50  100  200  500ng  Q     A

Q: pooled Q-sepharose eluate
A: Autoplex (25 FECU units per ml)

FACTOR IXA FOR THE TREATMENT OF BLEEDING DISORDERS

This application claims priority to U.S. provisional application 60/554,726, filed Mar. 19, 2004.

FIELD OF THE INVENTION

This invention relates to the treatment of blood coagulation pathologies by pharmaceutical preparations containing Factor IXa.

BACKGROUND OF THE INVENTION

Blood coagulation is a complex and dynamic biological process that depends on a series of interdependent biochemical reactions. In each step of the series, an active protease is generated from an inactive precursor. Each newly generated protease, in turn, acts on its substrate, another precursor protease, to generate a cascading reaction. This cascade produces ultimately sufficient active thrombin to generate a stable clot.

The terminal portion of this cascade occurs on phospholipid membrane of a platelet. On this surface, Factor IXa (activated by Factor XIa or VIIa, illustrated in FIG. 1), and in the presence of its co-Factor, Factor VIII, activates Factor X to Factor Xa. Factor Xa activates prothrombin to thrombin, which then activates fibrinogen to form the fibrin clot. Factor VIII's specific role is to enhance Factor IXa's catalysis of Factor X, as Factor IXa alone can only slowly activate Factor X in vitro. (van Dieijen et al, J Biol Chem. 1981 Apr. 10;256 (7):3433-42).

The most common blood coagulation pathology, Hemophilia A, is the X linked hereditary deficiency that leads to reduced levels of circulating Factor VIII in the blood of afflicted individuals. Concentrated Factor VIII preparations are used to treat such individuals to restore their circulating FVIII levels to functional levels. However, in approximately 20% of these patients, inhibitory allo-antibodies are produced against FVIII, abrogating the effectiveness of this treatment.

Treatment of patients that have become refractory to replacement FVIII therapy include immune tolerance induction (ITI), replacement therapy with Porcine FVIII, and a variety of preparations that are said to bypass the requirement for FVIII treatment in clotting. These bypassing preparations include recombinant FVIIa, Prothrombin Complexes Concentrates and activated Prothrombin Complex Concentrates (aPCCs).

The therapeutically effective substances in aPCCs have been speculated to be various combinations of the following factors: Thrombin, Factor VIIa, Factor IXa, Factor Xa, Factor XIa, Factor XIIa, Prothrombin/Factor Xa complex. However, the precise in vivo mechanism of action for aPCCs is still controversial.

SUMMARY OF THE INVENTION

This invention provides a method for treating bleeding disorders in a subject by administering a preparation enriched for Factor IXa. In one embodiment, the pharmaceutical preparation contains at least 10% Factor IXa (mg Factor IXa/mg total protein). Factor IXa for use in the present invention can be produced by proteolytically activating recombinantly-produced Factor IX. The cDNA coding for Factor IX has been isolated, characterized, and cloned into expression vectors. For example, Choo et al., Nature 299:178-180 (1982); Fair et al., Blood 64:194-204 (1084) and Kurachi et al., Proc. Nat. Acad. Sci. USA 79:6461-6464 (1982). A recombinant Factor IX has been produced by recombinant techniques, as described in U.S. Pat. No. 4,770,999, Kaufmann et al., Sep. 13, 1988, which is hereby incorporated by reference. The invention also provides a method for preparing and isolating Factor IXa from a plasma fraction such as Cohn Fraction IV.1 paste. It is accomplished by deliberately catalyzing the conversion of Factor IX to Factor IXa and introducing an anion exchange step, as a modification to the existing procedures, (described in U.S. Pat. Nos. 3,560,475 and 4,286,056) to selectively purify Factor IXa from the impurities present. This preparation, enriched for Factor IXa, is able to correct the Factor VIII bleeding phenotype of Factor VIII-deficient mice (fviii–/– mice). Furthermore, an additional utility of the invention is that it removes prekalikrein (PKA) activity from the starting material of Autoplex-T.

BRIEF DESCRIPTION OF THE DRAWINGS

FIG. 4A is a coomassie blue stained SDS-PAGE gel showing that at increasing concentrations of Factor XIa, more activated Factor IX is produced. Purified standards of Factor IXa and Factor IX were resolved on the same gel for comparison.

DETAILED DESCRIPTION OF THE INVENTION

Figure 1:
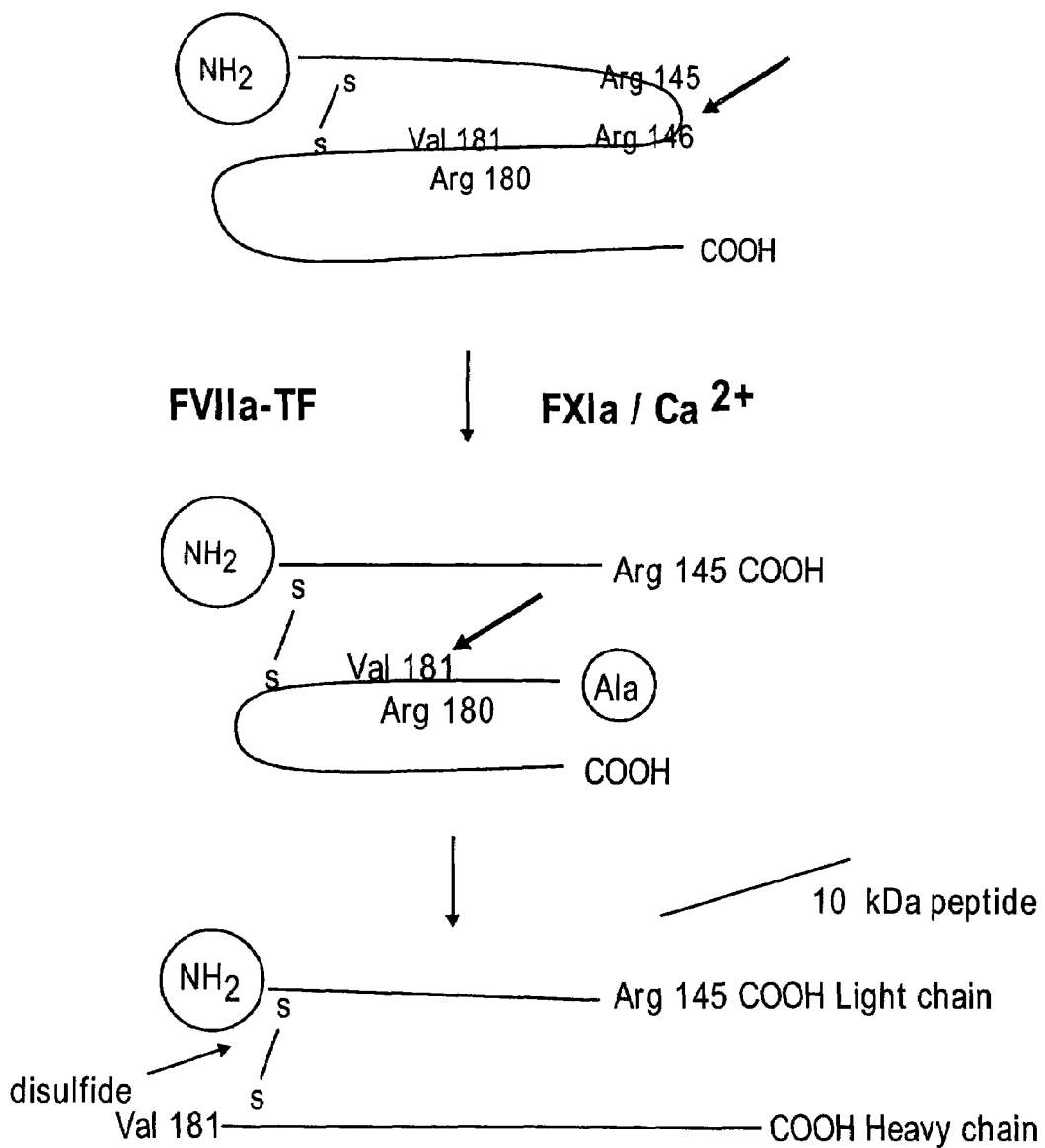
FIG. 1 shows the activation of Factor IX by Factor XIa and Calcium or Factor VIIa-tissue factor, which results in cleavage of an Arginine (Arg) Alanine (Ala) bond and the formation of Factor IXα, an inactive intermediate of Factor IXa. Cleavage of a second bond, Arg 180-Valine 181 (Val) results in the formation of Factor IXαβ, the active form of Factor IX (referred to as Factor IXa) and the release of a peptide fragment of approximately 10 kDa. (Figure modified from Royal A McGraw et al Clinics in Haematology—Vol 14.2 June 1985.) The immunoblot experiments used in subsequent figures employ sodium dodecyl sulphate polyacrylamide gel electrophoresis (SDS-PAGE) to resolve proteins in specific preparations. As these gels were run under reducing conditions, the disulfide bond holding the heterodimer together is broken and the heavy and light chains of Factor IX resolve as discrete species. For example, in the case of Factor IXαβ, the heavy and light chains will resolve at approximately 30 and 20 kDA respectively. In this strategy, concentration of the catalytic enzymes would be significantly lower than Factor IX facilitating their subsequent removal by an additional chromatographic, such as an monoclonal affinity column for Factor IX.

The invention provides a method of treating a subject with a bleeding disorder by administering a pharmaceutical preparation containing concentrated FIXa, which does not contain detectable PKA activity. Surprisingly, the FIXa initiates clotting in a subject without endogenous FVIII or with an endogenous form of FVIII that is inactive.

To make the Factor IXa concentrate, the starting material can be recombinantly-produced Factor IX, as provided in U.S. Pat. No. 4,770,999, which is herein incorporated by reference. Briefly, recombinant Factor IX at 114 μg/ml (2 μM) is incubated at 37° C. with 2.4 μg per ml (30 nM) Factor buffered Saline at 7.4 that contains 5 mM $CaCl_2$. This reaction is allowed to digest at 37° C. for two hours. Alternatively, recombinant Factor IX at 114 μg/ml (2 μM) is incubated with both Factor VIIa and Tissue Factor at 1 μg per ml (20 nM) at 37° C. in Tris buffered saline that contains 5 mM $Ca^{2+}$ and 1 mM Phospholipid vesicles. This reaction is allowed to digest for two hours. Both reaction conditions are adapted from Zhong et al, Proc Natl Acad Sci USA. 1994 Apr. 26;91(9): 3574-8. Furthermore, in both activation reactions an aliquot is removed, added to an equal volume of 2× reducing SDS-PAGE sample buffer and resolved on 10% polyacrylamide gels to ensure that Factor IX is converted quantitatively to Factor IXa. The preparation of activated Factor IX is diluted into heparinized citrate saline in individual aliquots that are suitable for administration to a mammalian subject. If desired, the catalysts, Factor XIa or TF/Factor VIIa could be removed by selectively purifying Factor IXa using an anti-FIX:Mg(II) IgG-Sepharose 4B column (1 mg of IgG/ml of gel) as described in Wojcik et al, Biochem. J. (1997) 323 (629-636). Bound FIXa is eluted from the column by a buffer containing 50 mM Tris EDTA Acetate (pH 7.5), 150 mM NaCl, 10 mM benzamidine and 10 mM EDTA. The eluted Factor IXa is subsequently dialyzed into a buffer containing heparinized citrate saline and aliquoted into concentrations suitable for administration to a mammalian subject.

To make the Factor IXa concentrate, the starting material can also be Cohn plasma fraction IV-1 precipitate. The precipitate is dissolved in saline to a concentration of 10% weight/volume at about 20° C. and then partially purified by adsorption onto tribasic calcium phosphate, as described in U.S. Pat. No. 3,560,475.

The tribasic calcium phosphate eluant is further purified and concentrated by polyethylene glycol (PEG) precipitation as discussed in U.S. Pat. No. 3,560,475. The resulting precipitate is dissolved in a 0.2 M sodium citrate solution and adjusted for pH as described in U.S. Pat. No. 4,286,056.

Silica at a concentration of 0.5 mg/ml is used to activate Factor XI to Factor XIa. Factor XI is a constituent of Fraction IV.1 pastes. Factor XIa activates Factor IX in the paste to Factor IXa.

The bulk solution containing activated Factor IXa is then purified further and concentrated on a Q-sepharose resin. The flow through is discarded and the bound proteins are eluted using a sodium citrate solution with a gradient of increasing NaCl concentration. Appropriate tests of the eluant fractions are then performed. The fractions containing the highest concentration of Factor IXa are pooled. This Q-sepharose fraction is enriched for Factor IXa and devoid of PKA activity.

Figure 2:
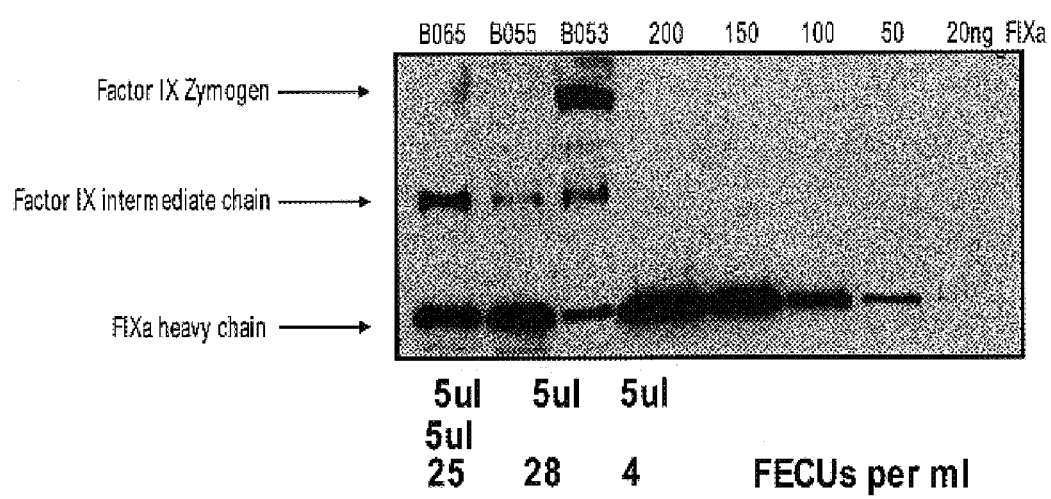
FIG. 2 is an immunoblot that measures the amount of activated Factor IX in specific Autoplex-T preparations using a monoclonal antibody specific to the heavy chain of Factor IX. The indicated amounts of purified activated Factor IXa were loaded on the gel. Five µl of each Autoplex-T preparation was loaded on each lane. Therefore, the approximate concentration of activated Factor IX in 2839B065 and 2839B055 lies somewhere between 20 and 50 ng/µl. The Factor Eight Correction Unites (FECUs) for each Autoplex-T preparation (Lot numbers. 2839B065, 2839B055, 2839B053) is indicated below the appropriate lane. These results also indicate that the amount of activated Factor IX correlates positively with FECU potency.

The invention was made after a biochemical characterization of an aPCC, Autoplex-T, revealed that it contains unexpectedly a high concentration of activated Factor IX (20-50 μg per ml). Furthermore, the concentration of activated Factor IX correlates with the Factor Eight Correction Unit Activity (FECU) of Autoplex-T (FIG. 2). The FECU activity assay measures how quickly an Autoplex preparation clots Factor VIII deficient plasma (described in U.S. Pat. No. 4,286,056). This assay is used to assign the potency of the Autoplex-T product, as it is thought to mimic the clinical utility of Autoplex-T: namely the ability to bypass the requirement for Factor VIII in clotting.

Figure 3:
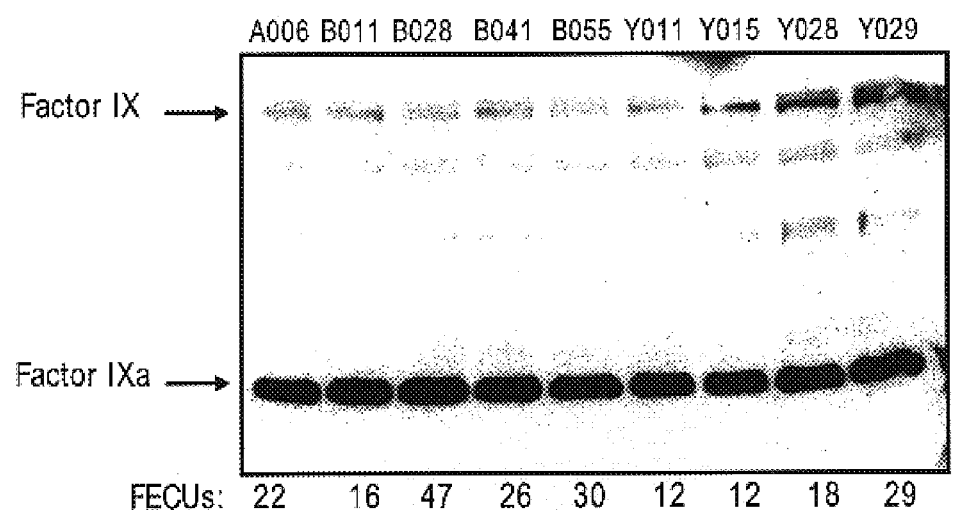
FIG. 3 is an Immunoblot with a monoclonal antibody specific to the heavy chain of Factor IX using a panel of Autoplex-T manufacturing lots produced in 2002 and 2003 that had above the minimum acceptable potency (>than 6 FECU units per ml). The Factor Eight Correction Units (FECUs) for each Autoplex-T preparation is indicated below the appropriate lane. In all cases, Factor IX has been activated to Factor IXa.
Figure 4A:
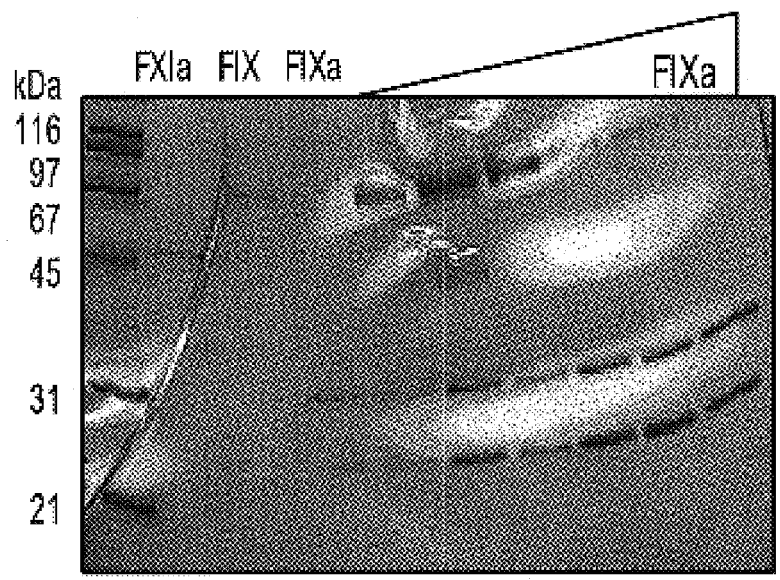
FIGS. 4A & B show a dose response of purified activated Factor IX in a FECU clotting assay. In this experiment, increasing amounts of Factor XIa (0, 10, 20, 30, 50 and 75 ng per ml) are used to regulate the amount of activated Factor IXa that was subsequently used in a FECU clotting assay.
Figure 4B:
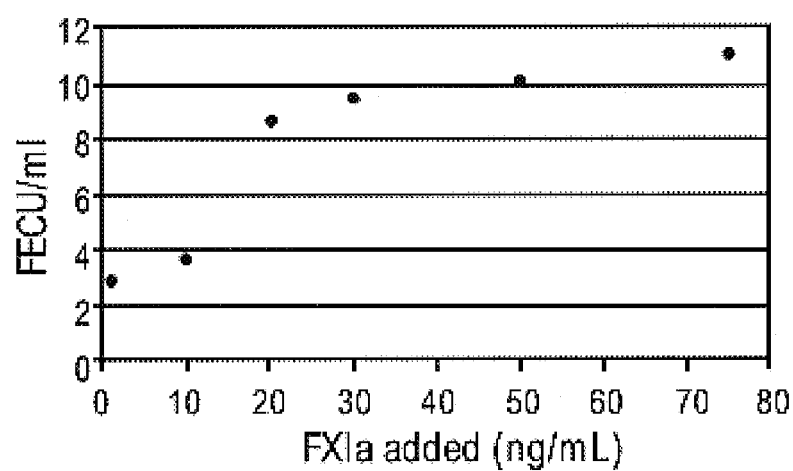
FIG. 4B Each aliquot of the digest was then analyzed by an activated partial thromboplastin time assay of FVIII deficient plasma. The amounts of Factor XIa (0-75 ng/ml) added do not have significant FECU activity in this experiment. These results show that activated Factor IX has Factor VIII bypassing activity.
Figure 5A:
FIG. 5A is a schematic demonstrating the purification scheme for purifying Factor IXa from Autoplex-T preparations.
Figure 5A:
Figure 5B:
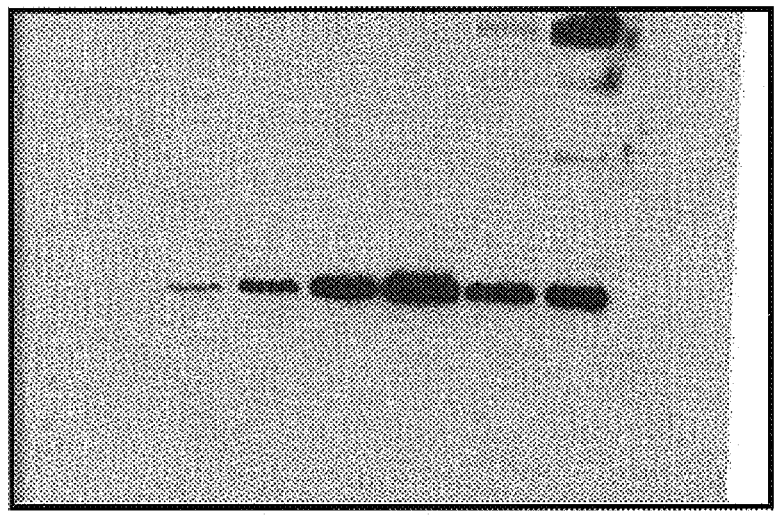
FIG. 5B demonstrates by immunoblot (with a monoclonal antibody specific for the heavy chain of Factor IX) that the concentration of activated Factor IX in the pooled Q-sepharose eluate is similar to an Autoplex-T preparation.

FIGS. 2 and 3 demonstrate that in multiple manufacturing lots of Autoplex-T, Factor IX is activated to Factor IXa. The correlation between the Factor IXa content of Autoplex and FECU activity indicates that Factor IXa could be the active pharmaceutical ingredient of Autoplex. FIG. 4 demonstrates that purified Factor IXa corrects the clotting time of Factor VIII deficient plasma in a dose-dependent fashion, consistent with this notion. To evaluate this hypothesis, we prepared a more purified preparation of Factor IXa from Autoplex-T using an anion exchange chromatographic step: Q-sepharose (FIGS. 5A and 5B). We then compared the biological efficacy of this preparation using a bleeding study in mice deficient for the fviii –/– gene. The results (Tables 3 and 4) show that the purified Factor IXa preparation is able to rescue the bleeding phenotype of these hemophiliac mice.

Autoplex-T contains significant amounts of PreKallikrein Activity, due the presence of βFXIIa, a proteolytic fragment of Factor XII. PKA activity is a labeled undesirable attribute of Autoplex-T, as it is associated with significant clinical symptoms, such as pain and hypotension. An additional utility of the invention is that purification of Factor IXa on the Q-sepharose column substantially removes PKA activity from the preparation (Table 1).

The following examples refer to the initial isolation of such a preparation of Factor IXa and the demonstration that it is effective in treating bleeding disorders.

EXAMPLE I

Sufficient amount of Fraction Cohn fraction IV-1 precipitate was suspended in 0.9% saline to make a 10% solution w/v. manufactured in typical fashion as described in U.S. Pat. Nos. 3,560,475 and 4,286,056. The pH was adjusted to 7.2 with 1N sodium hydroxide, creating sediment. After centrifugation, calcium phosphate was added to the supernatant. The solution was mixed and centrifuged to recover the calcium phosphate—adsorbed precipitate. The precipitate was resuspended in 0.1 M sodium citrate with a volume equal to 4% of the suspended IV-1 paste volume. The suspension was centrifuged and the supernatant, containing the coagulation Factors, was recovered.

EXAMPLE II

This supernatant was adjusted to with 0.5 g/L silica for the time determined to reach a Factor XIa level of about 0.02 U/ml as measured by the S-2222 peptide based chromogenic assay with an aliquot described above. The activation was terminated by filtration of the mixture through a 1.5 micron filter.

EXAMPLE III

The product from Example II was purified further by polyethylene glycol (PEG) precipitation. First, the solution was brought to 5% w/v PEG by the addition of PEG solid with an average molecular weight of 4000. The suspension was centrifuged, the pH of the supernatant was adjusted to 5.2 with 1N hydrochloric acid, then brought to a 20% w/v solution of PEG by the addition of additional PEG solid. This suspension was centrifuged, the precipitate dissolved in a 0.02 M sodium citrate solution containing 0.72% sodium chloride and 1.5 units heparin/ml (hereafter referred to as heparinized citrated saline), and the pH adjusted to 7.0. The potency of this material was determined to be 23 FECU units per ml.

In the FECU assay, one unit of FECU is defined as that quantity of activated prothrombin complex diluted 1:20 which, upon addition to an equal volume of Factor VIII deficient or FVIII-inhibitor-containing plasma, will correct the clotting time (ellagic acid—activated partial thromboplastin time) to 35 seconds (normal).

EXAMPLE IV

A sterile column was packed with Q-Sepharose Fast Flow™ (Amersham Biosciences). The column was equilibrated with sterile heparinized citrated saline, containing 0.025 M NaCl. After application of the product from Example III, the column was washed with the same buffer. Factor IXa was eluted with heparinized citrated saline containing increasing amounts of NaCl from 0.025 to 0.25 M. Samples were taken at intervals during the elution and those with the highest concentration of Factor IXa, as determined by immunoblot were pooled. This pool was then subsequently diluted in heparinized citrated saline, pH 7.0 to control for the increase in concentration during the chromatography. (Small aliquots of the bulk were diluted with heparinized citrated saline and tested for Factor VIII correction activity to determine what dilution would bring the potency levels down to 23 FECU/ml (potency of the starting material). The amount of activated Factor IXa in the preparation was determined by immunoblot (FIG. 4b) and shown to be similar to an Autoplex-T preparation.

Kallikrein (plasma kallikrein) is an enzyme that is involved in converting kininogen into kinins, which in turn may promote hypotension and associated undesired symptoms in a patient. Prekallikrein activator (PKA) is an enzyme that converts prekallikrein to kallikrein. The CBER reference used as a standard for the PKA assay lists beta-factor XIIa as a component of PKA (CBER Laboratory of Standards and Testing DMPQ/CBER/FDA Product Informatiom Circular for Reference Prekallikrein Activator (PKA) lot #3, date printed Mar 31, 1999). Prekallikrein activator (PKA) concentration was measured in Autoplex-T and in the purified FIXa preparation using a chromogenic assay (Tankersley et al; *Blood,* 62 (2): 448=-456, 1983).

Table 1 shows that the PKA activity is removed from the preparation by introduction of the Q-sepharose step. The PKA activity is presented as a percentage of the Center for Biologics Evaluation and Research Standard (CBER). The results indicate that the majority of the PKA activity in the starting material is not recovered in the Q-sepharose eluate.

TABLE 1

| Sample | Autoplex-T | Flow Through Q | Pooled Q-eluate |
|---|---|---|---|
| PKA activity % | >675% | >675% | Not detectable |

EXAMPLE V

The following describes the experimental protocol that evaluates bleeding and clotting in fviii −/− mice. Aliquots of test samples were frozen to −70 degrees C. in heparinized citrate saline, and used upon rapid thawing. Groups of five fviii −/− mice were injected with increasing doses of either Factor IXa or anti-inhibitor coagulant complex, Autoplex-T. The Factor IXa groups were injected with the following doses of activated Factor IX 0.002 µg/g, 0.01 µg/g, 0.02 µg/g, 0.13 µg/g, or 0.26 µg/g. The Autoplex-T groups were injected with 0.01 FECU/g, 0.075 FECU/g, or 0.150 FECU/g as a positive control. Five fviii −/− mice were injected with sterile heparinized citrated saline. Following a 30-minute incubation period for all mice, a lateral tail vein bleeding study was performed. Specifically, an incision was made on the lateral tail vein and the amount of blood that was discharged was collected during a thirty-minute period. At the end of this period the wound was cauterized to prevent lethality due to excessive blood loss. In addition, an incision was made to a group of 14 fviii −/− mice without any treatment and the amount of blood that was collected at specific time points was measured.

The evaluation of the hemostatic efficacy of these preparations would be best evaluated by measuring mouse lethality due to bleeding. Methods that measure hemostasis by recording blood loss within in a given time period are beset by a high variation in bleeding rates from mouse to mouse, as the results in Table 3 demonstrate. However, to avoid unnecessary mouse lethality, we designed the assay to look for clear evidence of hemostasis in individual mice treated with these preparations, with the understanding that not every mouse in each treated group would stop bleeding within the thirty minutes time frame that blood loss was recorded.

TABLE 2

Experimental protocol for evcaluation the ability of a negative control (HCS), Autoplex-T and Purified Factor IXa for correcting the bleeding phenotype of fvii −/−mice.

| A) FVIII-/- (14 mice) B) HCS vehicle (5 mice) C) Autoplex-T (15 mice) D) Purified Factor IXa (25 mice) | initiate tail bleed → | Assay by volume of blood lost and hemoglobin concentration |
|---|---|---|

Autoplex-T

| Group | 1 | 2 | 3 |
|---|---|---|---|
| Dose | 0.01 FECU/g | 0.075 FECU/g | 0.150 FECU/g |
| No. of mice | 5 | 5 | 5 |

Factor IXa

| Group | 1 | 2 | 3 | 4 | 5 |
|---|---|---|---|---|---|
| Dose | 0.002 µg/g | 0.01 µg/g | 0.02 µg/g | 0.13 µg/g | 0.26 µg/g |
| No of mice | 5 | 5 | 5 | 5 | 5 |

TABLE 3

Amount of blood volume lost and Hemoglobin concentrations in fviii −/− mice

| Mouse # | Genotype | Time Elapsed | Product Used | Conc. | Amt of Blood Loss | Hemoglobin |
|---|---|---|---|---|---|---|
| 14'35 | Hemophilic | 5 min | None | N/a | 340 μL | 14.2 g/dL |
| 14'37 | Hemophilic | 5 min | None | N/a | 200 μL | 14.7 g/dL |
| 14'39 | Hemophilic | 5 min | None | N/a | 400 μL | 14.7 g/dL |
| 14'50 | Hemophilic | 5 min | None | N/a | 80 μL | 9.8 g/dL |
| 14'51 | Hemophilic | 5 min | None | N/a | 78 μL | 10.3 g/dL |
| 14'53 | Hemophilic | 5 min | None | N/a | 80 μL | 10.2 g/dL |
| 12'10 | Hemophilic | 15 min | None | N/a | 300 μL | 14.5 g/dL |
| 14'5 | Hemophilic | 15 min | None | N/a | 100 μL | 12.2 g/dL |
| 14'55 | Hemophilic | 15 min | None | N/a | 125 μL | 13.6 g/dL |
| 12'7 | Hemophilic | 30 min | None | N/a | 100 μL | 13.2 g/dL |
| 12'6 | Hemophilic | 30 min | None | N/a | 65 μL | 7.6 g/dL |
| 12'9 | Hemophilic | 30 min | None | N/a | 75 μL | 8.7 g/dL |
| 14'11 | Hemophilic | 30 min | None | N/a | 350 μL | 17.6 g/dL |
| 14'14 | Hemophilic | 30 min | None | N/a | 250 μL | 17.8 g/dL |

As can be seen from the results of Table 3, Factor VIII deficient mice bleed when an incision is made in their tails. The amount of blood collected from each mouse is variable and ranges from 65 μl to 400 μl.

TABLE 4

Results of tail bleeding study

| Mouse # | Genotype | Time | Product | Conc. | Amt of Blood Loss | Hemoglobin |
|---|---|---|---|---|---|---|
| 1 | Normal | 30 min | None | N/a | 5 μL | 3.9 g/dL |
| 2 | Normal | 30 min | None | N/a | 10 μL | 4.0 g/dL |
| 3 | Normal | 30 min | None | N/a | 80 μL | 12.4 g/dL |
| 4 | Normal | 30 min | None | N/a | 5 μL | 0 g/dL |
| 5 | Normal | 30 min | None | N/a | 0 μL | 0 g/dL |
| 14'18 | Hemophilic | 30 min | Factor IXa | 0.26 μg/g | 275 μL | 16.6 g/dL |
| 14'16 | Hemophilic | 30 min | Factor IXa | 0.26 μg/g | 400 μL | 17.6 g/dL |
| 14'12 | Hemophilic | 13 min 30 sec | Factor IXa | 0.26 μg/g | 500 μL * | 14.9 g/dL |
| 14'89 | Hemophilic | 30 min | Factor IXa | 0.26 μg/g | 180 μL | 9.9 g/dL |
| 14'81 | Hemophilic | 30 min | Factor IXa | 0.26 μg/g | 395 μL | 17.6 g/dL |
| 14'75 | Hemophilic | 30 min | Factor IXa | 0.13 μg/g | 395 μL | 16.7 g/dL |
| 14'76 | Hemophilic | 30 min | Factor IXa | 0.13 μg/g | 70 μL | 16.0 g/dL |
| 14'72 | Hemophilic | 30 min | Factor IXa | 0.13 μg/g | 250 μL | 13.1 g/dL |
| 14'91 | Hemophilic | 30 min | Factor IXa | 0.13 μg/g | 300 μL | 13.5 g/dL |
| 14'87 | Hemophilic | 30 min | Factor IXa | 0.13 μg/g | 425 μL | 14.2 g/dL |
| 14'15 | Hemophilic | 30 min | Factor IXa | 0.02 μg/g | 5 μL ** | 3.8 g/dL |
| 14'70 | Hemophilic | 30 min | Factor IXa | 0.02 μg/g | 205 μL | 14.0 g/dL |
| 14'2 | Hemophilic | 30 min | Factor IXa | 0.02 μg/g | 0 μL ** | 0 g/dL |
| 14'28 | Hemophilic | 30 min | Factor IXa | 0.02 μg/g | 415 μL | 15.7 g/dL |
| 14'27 | Hemophilic | 30 min | Factor IXa | 0.02 μg/g | 200 μL | 13.9 g/dL |
| 14'86 | Hemophilic | 30 min | Factor IXa | 0.01 μg/g | 375 μL | 18.0 g/dL |
| 14'73 | Hemophilic | 30 min | Factor IXa | 0.01 μg/g | 75 μL | 14.5 g/dL |
| 14'77 | Hemophilic | 30 min | Factor IXa | 0.01 μg/g | 75 μL | 15.7 g/dL |
| 14'74 | Hemophilic | 30 min | Factor IXa | 0.01 μg/g | 16 μL ** | 5.8 g/dL |
| 14'88 | Hemophilic | 30 min | Factor IXa | 0.01 μg/g | 205 μL | 11.3 g/dL |
| 14'67 | Hemophilic | 30 min | Factor IXa | 0.002 μg/g | 425 μL | 15.3 g/dL |
| 14'68 | Hemophilic | 30 min | Factor IXa | 0.002 μg/g | 175 μL | 13.6 g/dL |
| 14'19 | Hemophilic | 30 min | Factor IXa | 0.002 μg/g | 0 μL ** | 0 g/dL |
| 14'10 | Hemophilic | 30 min | Factor IXa | 0.002 μg/g | 75 μL | 14.0 g/dL |
| 14'80 | Hemophilic | 30 min | Factor IXa | 0.002 μg/g | 160 μL | 13.8 g/dL |
| 13'70 | Hemophilic | 30 min | Autoplex | 0.150 FECU/g | 35 μL ** | 9.3 g/dL |
| 14'30 | Hemophilic | 30 min | Autoplex | 0.150 FECU/g | 370 μL | 15.8 g/dL |
| 12'78 | Hemophilic | 15 min | Autoplex | 0.150 FECU/g | 500 μL | Not measured |
| 14'98 | Hemophilic | 30 min | Autoplex | 0.150 FECU/g | 300 μL | 15.4 g/dL |
| 12'83 | Hemophilic | 30 min | Autoplex | 0.150 FECU/g | 195 μL | 12.3 g/dL |
| 13'3 | Hemophilic | 30 min | Autoplex | 0.075 FECU/g | 250 μL | 19.0 g/dL |
| 13'6 | Hemophilic | 30 min | Autoplex | 0.075 FECU/g | 30 μL ** | 11.9 g/dL |
| 13'21 | Hemophilic | 30 min | Autoplex | 0.075 FECU/g | 400 μL | 18.4 g/dL |
| 13'53 | Hemophilic | 30 min | Autoplex | 0.075 FECU/g | 400 μL | 18.7 g/dL |
| 13'28 | Hemophilic | 30 min | Autoplex | 0.075 FECU/g | 80 μL | 15.4 g/dL |
| 14'71 | Hemophilic | 30 min | Autoplex | 0.01 FECU/g | 225 μL | 13.2 g/dL |
| 14'78 | Hemophilic | 30 min | Autoplex | 0.01 FECU/g | 375 μL | 16.5 g/dL |

TABLE 4-continued

Results of tail bleeding study

| Mouse # | Genotype | Time | Product | Conc. | Amt of Blood Loss | Hemoglobin |
|---|---|---|---|---|---|---|
| 14'82 | Hemophilic | 30 min | Autoplex | 0.01 FECU/g | 300 μL | 16.8 g/dL |
| 14'79 | Hemophilic | 30 min | Autoplex | 0.01 FECU/g | 60 μL ** | 14.3 g/dL |
| 14'90 | Hemophilic | 30 min | Autoplex | 0.01 FECU/g | 475 μL | 16.0 g/dL |
| 13'55 | Hemophilic | 30 min | Heparinized Saline | N/a | 170 μL | 17.5 g/dL |
| 14'22 | Hemophilic | 30 min | Heparinized Saline | N/a | 375 μL | 14.0 g/dL |
| 14'23 | Hemophilic | 30 min | Heparinized Saline | N/a | 185 μL | 13.9 g/dL |
| 14'24 | Hemophilic | 30 min | Heparinized Saline | N/a | 280 μL | 15.1 g/dL |
| 14'25 | Hemophilic | 30 min | Heparinized Saline | N/a | 125 μL | 14.2 g/dL |

\* The mouse was cauterized early due to excessive bleeding
\*\* The volume is below the lower range of blood lost by fviii−/− deficient animals.

In contrast to the hemophiliac mice of Table 3, when a lateral tail vein bleed is performed on wild type mice as shown in Table 4 they are able to form a clot as indicated by the low volume of blood collected (0 to 80 μls).

Factor IXa, at three of the lower dosages, was able to correct bleeding phenotype of specific fviii −/− mice. In four out of 15 mice at these three doses, the amount of blood lost was less than the lower range of 65 μls, and consistent with the amount of blood lost measured in the wild type animals (0 to 80 μls). These instances provide clear evidence that bleeding has been stopped efficiently by the Factor IXa preparation. Similarly, for three out of 15 mice, Autoplex-T was able to restore hemostasis to wild type levels. The technician who performed the studies also noted that a partial hemostatic plug had formed in those Autoplex and Factor IXa treated mice that did not show evidence of hemostasis by the blood loss assay. Consequently, these results indicate that Factor IXa has similar in vivo efficacy to the commercial product Autoplex-T.

Interestingly, at two of the higher doses of Factor IXa and the highest dose of Autoplex-T, bleeding appeared to increase, consistent with these agents causing Disseminated Intra-Vascular Coagulation (DIC). This is not surprising, as DIC is a well-recognized complication of higher doses of bypassing therapies.

These results provide clear evidence that Factor IXa has biological efficacy in treating bleeding disorders: It reduced bleeding to wild type levels in specific mice and its spectrum of efficacy was comparable to the current commercial bypassing therapy Autoplex-T. Factor IXa is therapeutically active between 0.002 μg and 0.02 μg per g of body weight of treated mice. Based upon these results Factor IXa could be dosed in patients between 2 and 20 mg per kg of body weight.

Given the present disclosure, one of skill in the art will naturally think of additional embodiments of the invention, and the following claims are not intended to limit the scope of the invention.

We claim:

1. A method of treating a subject with a bleeding pathology, said method comprising administering a pharmaceutical preparation comprising a pharmaceutically acceptable carrier containing a therapeutically effective protein, the therapeutically effective protein consisting essentially of Factor IXa, wherein the amount of Factor IXa is at least 10% mg Factor IXa/mg total protein, wherein said pharmaceutical preparation contains little or no prekallikrein activator activity.

2. The method of claim 1 wherein said bleeding pathology is caused by the presence of FVIII inhibitors in the subject's blood.

3. The method of claim 1 wherein said bleeding pathology is caused by the absence of endogenous FVIII activity in the subject's blood.

4. The method of claim 1 wherein said bleeding pathology is caused by the absence of endogenous FIX activity in the subject's blood.

\* \* \* \* \*